US007858098B2

(12) United States Patent
Dubin et al.

(10) Patent No.: US 7,858,098 B2
(45) Date of Patent: *Dec. 28, 2010

(54) VACCINE

(75) Inventors: Gary Dubin, King of Prussia, PA (US);
Bruce Innis, King of Prussia, PA (US);
Moncef Mohammed Slaoui, King of Prussia, PA (US); Martine Anne Cecile Wettendorff, Rixensart (BE)

(73) Assignee: GlaxoSmithKline Biologicals, s.a., Rixensart (BE)

( * ) Notice: Subject to any disclaimer, the term of this patent is extended or adjusted under 35 U.S.C. 154(b) by 666 days.

This patent is subject to a terminal disclaimer.

(21) Appl. No.: 11/367,601

(22) Filed: Dec. 16, 2005

(65) Prior Publication Data

US 2007/0020288 A1    Jan. 25, 2007

Related U.S. Application Data

(63) Continuation-in-part of application No. 11/114,301, filed on Apr. 26, 2005, now abandoned, which is a continuation-in-part of application No. PCT/EP03/14562, filed on Dec. 18, 2003.

(60) Provisional application No. 60/435,035, filed on Dec. 20, 2002, provisional application No. 60/496,653, filed on Aug. 20, 2003.

(51) Int. Cl.
*A61K 39/12* (2006.01)
*A61K 39/295* (2006.01)

(52) U.S. Cl. .................................. 424/204.1

(58) Field of Classification Search ........................ None
See application file for complete search history.

(56) References Cited

U.S. PATENT DOCUMENTS

| | | | |
|---|---|---|---|
| 5,855,891 A | 1/1999 | Lowy et al. | |
| 6,066,324 A | 5/2000 | Gissmann et al. | |
| 6,245,568 B1 | 6/2001 | Volkin et al. | |
| 6,251,678 B1 | 6/2001 | Volkin et al. | |
| 6,908,613 B2 | 6/2005 | Wilson et al. | |
| 6,936,255 B1 | 8/2005 | Wettendorff | |
| 7,101,560 B2 | 9/2006 | Wettendorff | |
| 7,217,419 B2* | 5/2007 | Wettendorff | 424/204.1 |
| 7,416,846 B2* | 8/2008 | Wettendorff | 435/6 |
| 2004/0121465 A1 | 6/2004 | Robinson | |
| 2006/0177817 A1* | 8/2006 | Jansen et al. | 435/5 |
| 2006/0240040 A1* | 10/2006 | Bryan et al. | 424/204.1 |
| 2007/0036824 A1* | 2/2007 | Bryan et al. | 424/204.1 |
| 2008/0226660 A1* | 9/2008 | Bryan et al. | 424/184.1 |

FOREIGN PATENT DOCUMENTS

| | | |
|---|---|---|
| WO | WO 94/21292 | 9/1994 |
| WO | WO 95/17209 | 6/1995 |
| WO | WO 95/31532 | 11/1995 |
| WO | WO 96/11274 | 4/1996 |
| WO | WO 99/45957 | 9/1999 |
| WO | WO 99/50424 | 10/1999 |
| WO | WO 00/09699 | 2/2000 |
| WO | WO 00/23105 | 4/2000 |
| WO | WO 01/17550 | * 3/2001 |
| WO | WO01/97840 | 12/2001 |
| WO | WO03/077942 | 9/2003 |
| WO | WO 2004/056389 | 7/2004 |
| WO | WO2005/032586 | 4/2005 |

OTHER PUBLICATIONS

Almadori et al (Clinical Cancer Research 7:3988-3993, 2001).*
Smith et al (International Journal of Cancer 108:766-772, 2004).*
Koutsky et al (New England Journal of Medicine 347: 1645-1651, 2002).*
Suzich et al (Proceedings of the National Academy of Sciences USA 92:11553-11557, 1995).*
Moore et al (Journal of General Virology 83: 229902301, 2002).*
Zhehbe et al (Journal of Pathology 181:270-274, 1997).*
Giroglou et al., "Immunological Analyses of Human Papillomavirus Capsids", *Vaccine*, Butterworth Scientific, vol. 19, No. 13-14, pp. 1783-1793 (2001).
Clifford, et al., "Human Papillomavirus Types in Invasive Cervical Cancer Worldwide: A Meta-Analysis", *British Journal of Cancer*, vol. 88, pp. 63-73 (2003).
Munoz, et al., "Against Which Human Papillomavirus Types Shall We Vaccinate and Screen? The International Perspective", *Int. J. Cancer*, vol. 111, 278-285 (2004).
Bachtiary, et al, Impact of multiple HPV infection on response to treatment and survival in pts. receiving radical radiotherapy for cervical cancer, International Journal of Cancer, Journal International Du Cancer, US, Nov. 20, 2002, vol. 102, No. 3, pp. 237-243.
Balsley, J.F., et al, Progress in the development of human papillomavirus vaccines for HPV-11 and HPV-16/18 and mapping of a critical neutralizing epitope, 18th International Papillomavirus Conference 2000, Online 2000, XP002278802, Retrieved from Internet: www.hpv2000.com/idabstract.asp, retrieved on May 3, 2004.
Bass, et al, Progress in the search of a vaccine against human papilloma virus, IAVI Report Oct./Nov. 2002, Online, Oct. 10, 2002, retrieved from the Internet—www.aegis.com/pubs/iavi/2002/IAVI2002-1003.html, retrieved on Apr. 21, 2004.
Billich A, "HPV Vaccine Medimmune/ GlaxoSmithKline", Current Opinion in Invest. Drugs, vol. 4, No. 2, Feb. 2003, pp. 210-213.
Bosch, et al., Prevalence of human papillomavirus in cervical cancer: a worldwide perspective, J. Nat. Canc. Inst. vol. 87, No. 11, pp. 796-802 (1995).
Breitburd et al., Immunization with Virus-Like Particles from Cottontail Rabbit Papillomavirus (CRPV) Can Protect Against Experimental CRPV Infection, Journal of Virology, vol. 69, p. 3959-3963(1995).
Brown, et al, A dose ranging study of the safety and immunogenicity profiles of a quadrivalent HPV (types 6, 11, 16 and 18) L1 VLP candidate vaccine in young healthy women, Abstract 0-51, 19th International Papillomavirus Conference, Sep. 2001, Florianopolis, Brazil.

(Continued)

Primary Examiner—Mary E Mosher
(74) Attorney, Agent, or Firm—Gwynedd Warren; GlaxoSmithKline

(57) ABSTRACT

This invention pertains to methods for treating infections caused by human papillomaviruses. It has been determined that immunization with HPV16 and HPV 18 virus like particles provides cross-protection against other HPV types.

34 Claims, 2 Drawing Sheets

OTHER PUBLICATIONS

Figure 1A:
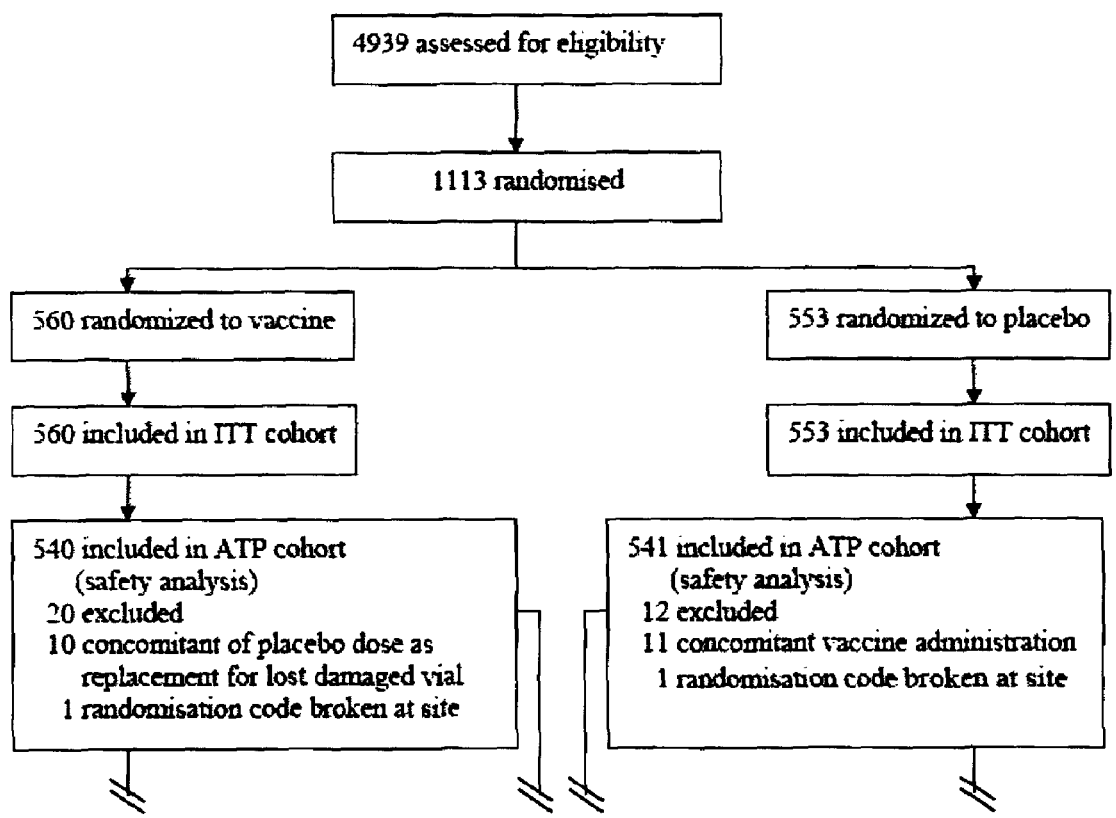

Carter, et al., Comparison of human papillomavirus Types 16, 18, and 6 capsid antibody responses following incident infection, The Journal of Infectious Diseases Society of America, vol. 181, pp. 19111-19119 (2000).

Chan, et al., Analysis of genomic sequences of 95 papillomavirus types: Uniting typing, phylogeny, and taxonomy, Journal of Virology, vol. 69, No. 5, pp. 3074-3083 (1995).

Chan, et al., Phylogenetic analysis of 48 papillomavirus types and 28 subtypes and variants: a showcase for the molecular evolution of DNA viruses, J. Virology, vol. 66, No. 10, pp. 5714-5725 (1992).

Christensen, N. D., et al., Monoclonal Antibodies to HPV-6 L1 Virus-Like Particles Identify Comformational and Linear Neutralizing Epitopes on HIV-11 in Addition to Type-Specific Epitopes on HPV-6, Virology, 1996, vol. 224, pp. 477-486.

Clifford, et al, Comparison of HPV type distribution in high-grade cervical lesions and cervical cancer: a meta-analysis, British J. of Cancer, vol. 89, pp. 101-105 (2003).

Clifford, et al., Human papillomavirus types in invasive cervical cancer worldwide: a meta-analysis, British J. of Cancer, vol. 88, pp. 63-73 (2003).

Combita, Alba-Lucia, et al, Identification of two cross-neutralizing linear epitopes within the L1 major capsid protein of human papillomaviruses, Journal of Virology, US, vol. 76, No. 13, Jul. 2002, pp. 6480-6486.

DeVilliers, E.M., et al: "Classification of Papillomaviruses," Virology, Academic Press, Orlando, cited in the application (the whole document), US, vol. 324, No. 1, Jun. 20, 2004, pp. 17-27.

Giroglou et al , "Immunological analyses of human papillomavirus capsids", Vaccine, vol. 19, No. 13-14, 2001, pp. 1783-1793 (2001).

GlaxoSmithKline HPV Vaccine Study Group, Harper et al., "Efficacy of a Bivalent L1 Virus-Like Particle Vaccine in Prevention of Infection with Human Papillomavirus Types 16 and 18 in Young Women: A Rand. Contr. Trial", The Lancet (Limited), vol. 364, No. 9447, Nov. 13, 2004, pp. 1757-1765.

Harro, et al., Safety and immunogenicity trial in adult volunteers of a human papillomavirus 16 L1 virus-like particle vaccine, J. of the National Cancer Institute, vol. 93, No. 4, pp. 284-292 (2001).

Moore, et al., Absence of canine oral papillomavirus DNA following prophylactic L1 particle-mediated immunotherapeutic delivery vaccination, Journal of General Virology 83:2299-2301, (2002).

Palker, et al. "Antibody, cytokine and cytotoxic T lymphocyte responses in chimpanzees immunized with human papillomavirus virus-like particles" Vaccine, Butterworth Scientific, 2001, 19(27), pp. 3733-3743.

Reinis, M., Technology Evaluation: HPV Vaccine (Quadrivalent), Aventis Pasteur, Current Opinion in Molecular Therapeutics, vol. 6, No. 2, Apr. 2004, pp. 206-211.

Roden, et al. "Assesment of the serological relatedness of genital human papillomaviruses by hemagglutination inhibition" J of Virology, The American Society for Microbiology, 1996, 70(5), pp. 3298-3301.

Schiller et al., Papillomavirus-like particles and HPV vaccine development, Seminars in Cancer Biology, vol. 7, No. 6, pp. 373-382 (1996).

Schiller, et al, Papillomavirus-like particle base vaccines: cervical cancer and beyond, Expert Opinion on Biological Therapy, Ashley, London, GB, vol. 1, No. 4, pp. 571-581 (2001).

Steller, et al., Cervical cancer vaccines: progress and prospects, Journal of the Society for Gynecologic Investigation, US, Sept., Oct. 2002, vol. 9, No. 5, pp. 254-264 (2002).

Thompson, et al , Immunogenicity & reactogenicity of a recombinant HPV6 fusion protein vaccine adjuvanted with monophosphoryl lipid A, Biochemical Society Transactions, vol. 274S p. 25 (1997).

Van Ranst, et al., Phylogenetic classification of human papillomaviruses: correlation with clinical manifestations, J. of General Virology, vol. 73, pp. 2653-2660 (1992).

Villa., et al, A dose-ranging safety and immunogenicity study of a quadrivalent HPV (type 6/11/16/18) L1 VLP vaccine in women, HPV Clinical Workshop & 20th International Papillomavirus Conference 2002, Oct. 4-9, 2002, Paris, Institute Pasteur.

Villa et al., "Prophylactic Quadrivalent Human Papillomavirus (Types 6, 11, 16 and 18) L1 Virus-Like Particle Vaccine in Prevention of Infection with Human Papillomavirus Types 16 and 18 in Young Women: A Rand. Controlled Trial", Lancet Oncology, vol. 6, No. 5, May 2005, pp. 271-278.

Wheeler, "Preventive vaccines for cervical cancer" *Salud Publica de Mexico*, 1997, 39(4), pp. 283-287.

White, et al., "*In Vitro* Infection and Type-Restricted Antibody-Mediated Neutralization of Authentic Human Papillomavirus Type 16, Journal of Virology", vol. 72, No. 2, pp. 959-964 (1998).

U.S. Appl. No. 09/807,657, filed Apr. 16, 2001, Garcon.
U.S. Appl. No. 10/983,451, filed Nov. 8, 2004, Wettendorff.
U.S. Appl. No. 11/477,879, filed Jun. 29, 2006, Slaoui, et al.

* cited by examiner

Continued

SEQUENCE LISTING

```
<160> NUMBER OF SEQ ID NOS: 2

<210> SEQ ID NO 1
<211> LENGTH: 471
<212> TYPE: PRT
<213> ORGANISM: Homo sapien

<400> SEQUENCE: 1

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
```

```
                    290                 295                 300
Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Asp Thr
                325                 330                 335

Thr Arg Ser Thr Asn Met Ser Leu Cys Ala Ala Ile Ser Thr Ser Glu
                340                 345                 350

Thr Thr Tyr Lys Asn Thr Asn Phe Lys Glu Tyr Leu Arg His Gly Glu
                355                 360                 365

Glu Tyr Asp Leu Gln Phe Ile Phe Gln Leu Cys Lys Ile Thr Leu Thr
370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Leu Glu Asp
                405                 410                 415

Thr Tyr Arg Phe Val Thr Ser Gln Ala Ile Ala Cys Gln Lys His Thr
                420                 425                 430

Pro Pro Ala Pro Lys Glu Asp Pro Leu Lys Lys Tyr Thr Phe Trp Glu
                435                 440                 445

Val Asn Leu Lys Glu Lys Phe Ser Ala Asp Leu Asp Gln Phe Pro Leu
450                 455                 460

Gly Arg Lys Phe Leu Leu Gln
465                 470

<210> SEQ ID NO 2
<211> LENGTH: 472
<212> TYPE: PRT
<213> ORGANISM: Homo sapien

<400> SEQUENCE: 2

Met Ala Leu Trp Arg Pro Ser Asp Asn Thr Val Tyr Leu Pro Pro Pro
1               5                   10                  15

Ser Val Ala Arg Val Val Asn Thr Asp Asp Tyr Val Thr Arg Thr Ser
                20                  25                  30

Ile Phe Tyr His Ala Gly Ser Ser Arg Leu Leu Thr Val Gly Asn Pro
            35                  40                  45

Tyr Phe Arg Val Pro Ala Gly Gly Asn Lys Gln Asp Ile Pro Lys
        50                  55                  60

Val Ser Ala Tyr Gln Tyr Arg Val Phe Arg Val Gln Leu Pro Asp Pro
65                  70                  75                  80

Asn Lys Phe Gly Leu Pro Asp Asn Ser Ile Tyr Asn Pro Glu Thr Gln
                85                  90                  95

Arg Leu Val Trp Ala Cys Val Gly Val Glu Ile Gly Arg Gly Gln Pro
            100                 105                 110

Leu Gly Val Gly Leu Ser Gly His Pro Phe Tyr Asn Lys Leu Asp Asp
        115                 120                 125

Thr Glu Ser Ser His Ala Ala Thr Ser Asn Val Ser Glu Asp Val Arg
    130                 135                 140

Asp Asn Val Ser Val Asp Tyr Lys Gln Thr Gln Leu Cys Ile Leu Gly
145                 150                 155                 160

Cys Ala Pro Ala Ile Gly Glu His Trp Ala Lys Gly Thr Ala Cys Lys
                165                 170                 175

Ser Arg Pro Leu Ser Gln Gly Asp Cys Pro Pro Leu Glu Leu Lys Asn
                180                 185                 190
```

-continued

```
Thr Val Leu Glu Asp Gly Asp Met Val Asp Thr Gly Tyr Gly Ala Met
        195                 200                 205

Asp Phe Ser Thr Leu Gln Asp Thr Lys Cys Glu Val Pro Leu Asp Ile
        210                 215                 220

Cys Gln Ser Ile Cys Lys Tyr Pro Asp Tyr Leu Gln Met Ser Ala Asp
225                 230                 235                 240

Pro Tyr Gly Asp Ser Met Phe Phe Cys Leu Arg Arg Glu Gln Leu Phe
                245                 250                 255

Ala Arg His Phe Trp Asn Arg Ala Gly Thr Met Gly Asp Thr Val Pro
                260                 265                 270

Pro Ser Leu Tyr Ile Lys Gly Thr Gly Met Arg Ala Ser Pro Gly Ser
        275                 280                 285

Cys Val Tyr Ser Pro Ser Pro Ser Gly Ser Ile Val Thr Ser Asp Ser
        290                 295                 300

Gln Leu Phe Asn Lys Pro Tyr Trp Leu His Lys Ala Gln Gly His Asn
305                 310                 315                 320

Asn Gly Val Cys Trp His Asn Gln Leu Phe Val Thr Val Val Asp Thr
                325                 330                 335

Thr Arg Ser Thr Asn Leu Thr Ile Cys Ala Ser Thr Gln Ser Pro Val
                340                 345                 350

Pro Gly Gln Tyr Asp Ala Thr Lys Phe Lys Gln Tyr Ser Arg His Val
        355                 360                 365

Glu Glu Tyr Asp Leu Gln Phe Ile Phe Gln Leu Cys Thr Ile Thr Leu
        370                 375                 380

Thr Ala Asp Val Met Ser Tyr Ile His Ser Met Asn Ser Ser Ile Leu
385                 390                 395                 400

Glu Asp Trp Asn Phe Gly Val Pro Pro Pro Thr Thr Ser Leu Val
                405                 410                 415

Asp Thr Tyr Arg Phe Val Gln Ser Val Ala Ile Thr Cys Gln Lys Asp
                420                 425                 430

Ala Ala Pro Ala Glu Asn Lys Asp Pro Tyr Asp Lys Leu Lys Phe Trp
        435                 440                 445

Asn Val Asp Leu Lys Glu Lys Phe Ser Leu Asp Leu Asp Gln Tyr Pro
        450                 455                 460

Leu Gly Arg Lys Phe Leu Val Gln
465                 470
```

VACCINE

CROSS-REFERENCE TO PREVIOUS APPLICATION

This application is a continuation-in-part of Ser. No. 11/114,301 filed 26 Apr. 2005 now abandoned, which is a continuation-in-part of PCT/EP2003/014562 filed 18 Dec. 2003, which claims the benefit of U.S. Provisional Applications Nos. 60/435,035, filed 20 Dec. 2002 and 60/496,653, filed 20 Aug. 2003.

FIELD OF THE INVENTION

The present invention relates to human papillomavirus (HPV) vaccines.

BACKGROUND OF THE INVENTION

Papillomaviruses are small DNA tumour viruses, which are highly species specific. So far, over 100 individual human papillomavirus (HPV) genotypes have been described. HPVs are generally specific either for the skin (e.g. HPV-1 and -2) or mucosal surfaces (e.g. HPV-6 and -11) and usually cause benign tumours (warts) that persist for several months or years. Such benign tumours may be distressing for the individuals concerned but tend not to be life threatening, with a few exceptions.

Some HPVs are also associated with cancers, known as oncogenic HPV types. The strongest positive association between an HPV and human cancer is that which exists between HPV-16 and HPV-18 and cervical carcinoma. Cervical cancer is the most common malignancy in developing countries, with about 500,000 new cases occurring in the world each year.

Other HPVs of particular interest with respect to cancer are types 31, 33, 35, 39, 45, 51, 52, 56, 58, 59, 66 and 68 (referred to as "oncogenic-HPV types"). Types 16 and 18 are those which have the highest association with cervical cancer. Types 31 and 45 are the types with the next highest association with a cancer risk (Munoz N, Bosch FX, de Sanjose S et al. International Agency for Research on Cancer Multicenter Cervical Cancer Study Group. *N Engl J Med* 2003; 348: 518-27.)

HPV virus like particles (VLPs) have been suggested as potential vaccines for treatment of HPV. Animal studies have shown that VLPs produce no cross protection against infection for other HPV types—see, for example Suzich, J. A., et al, Proc Natl Acad Sci, 92: 11553-11557, 1995, and Breitburd, Seminars in Cancer Biology, vol 9, 1999, pp 431-445.

WO2004/056389 discloses that an HPV 16, 18 VLP vaccine can provide cross protection against infection by HPV types other than 16 and 18. Statistically significant protection was observed against certain groups of HPV types. However, the level of cross protection against individual types within groups was not disclosed.

There is still a need for a vaccine that protects against multiple HPV types.

SUMMARY OF THE INVENTION

The present invention relates to a multivalent HPV vaccine, the vaccine comprising an L1 protein or immunogenic fragment thereof from at least 3 different oncogenic HPV types, those types including HPV 16 and HPV 18, wherein the vaccine does not comprise an L1 protein or immunogenic fragment thereof from an HPV type selected from the list consisting of HPV 31, HPV 45, HPV 52 or any combination thereof.

The present invention further relates to use of a composition comprising an L1 protein or immunogenic fragment thereof from HPV 16 and HPV 18 in the manufacture of a medicament for prevention of infection by one or more of the group consisting of HPV 31, HPV 45 and HPV 52.

The present invention further relates to use of a composition comprising an L1 protein or immunogenic fragment thereof from HPV 16 and HPV 18 in the manufacture of a medicament for prevention of cytological abnormalities, and/or reduction of the frequency of cytological abnormalities, and/or prevention of CIN lesions (CIN 1, CIN 2, CIN 3) in an individual, the abnormalities or lesions caused by at least one HPV type other than HPV 16 or HPV 18, suitably being caused by HPV type 31, or 45, or 52, or a combination thereof.

The invention further relates to a method of prevention and/or treatment of HPV infection and/or disease, the method comprising delivering to an individual in need thereof an effective amount of a composition comprising an L1 protein or immunogenic fragment thereof from at least 3 different oncogenic HPV types, those types including HPV 16 and HPV 18, wherein the vaccine does not comprise an L1 protein or immunogenic fragment thereof from an HPV type selected from the list consisting of HPV 31, HPV 45, HPV 52 or any combination thereof.

The invention also relates to a method for manufacture of a vaccine, the method comprising combining an L1 protein or immunogenic fragment thereof from at least 3 different oncogenic HPV types, those types including types HPV 16 and HPV 18, wherein the vaccine does not comprise an L1 protein or immunogenic fragment thereof from an HPV type selected from the list consisting of HPV 31, HPV 45, HPV 52 or any combination thereof.

DETAILED DESCRIPTION

The general existence of cross protection afforded by HPV 16 and HPV 18 against both incident and persistent infection, as assessed in relation to certain groups of HPV types, has been disclosed in WO2004/056389.

We have surprisingly discovered that the cross protection against certain (non HPV16, HPV 18) HPV types (as assessed by the efficacy of an HPV 16 and HPV 18 vaccine against those types), is higher than against certain other (non HPV 16, HPV 18) HPV types. Cross protection may be considered as the protection afforded by a vaccine containing one HPV type against infection (incident or persistent) and/or disease caused by a different HPV type. Cross protection may be assessed by considering the vaccine efficacy (V.E.), wherein the V.E. is the % improvement in protection against infection by the vaccine compared to a placebo group for a given type.

Such a finding has potential implications for vaccine design. For example, the level of cross protection afforded by HPV 16 and HPV 18 L1 containing vaccines against certain other HPV types, such as HPV 31, HPV 45 and HPV 52, allows L1 components from these HPV types to be omitted from a vaccine comprising HPV 16 and HPV18 while still providing a vaccine which provides some protection against incident and/or persistent infection and/or disease related to those omitted types.

After HPV types 16 (found in 53.5% of cervical cancer) and 18 (found in 17.2% of cervical cancer), types 45 (6.7%) and 31 (2.9%) are the next most significant in terms of their frequency in cervical cancers (Muñoz et al supra). HPV 33

(2.6%) is next, followed by HPV 52 (2.3%). Thus, when designing a multivalent HPV vaccine, types 31 and 45 would generally be included by the skilled person from a statistical perspective.

The ability to omit antigens from certain HPV types potentially allows inclusion of L1 protein from other HPV types, or indeed antigens from other viruses or pathogens, into a vaccine in a scenario where the total amount of antigen in a vaccine may be limited, for example by physical, chemical, regulatory or other constraints.

Vaccine Composition

In one aspect of the invention the vaccine does not contain an L1 protein or immunogenic fragment thereof from HPV 31.

In one aspect of the invention the vaccine is capable of providing protection against incident and for persistent HPV infection by HPV 31.

In one aspect of the invention the vaccine of the invention does not contain an L1 protein or immunogenic fragment thereof from HPV 45.

In one aspect of the invention the vaccine is capable of providing protection against incident and/or persistent HPV infection by HPV 45.

In one aspect of the invention the vaccine does not contain an L1 protein or immunogenic fragment thereof from HPV 52.

In one aspect of the invention the vaccine is capable of providing protection against incident and for persistent HPV infection by HPV 52.

In one aspect of the invention the vaccine of the invention does not contain an L1 protein or immunogenic fragment thereof from HPV 31 and 45.

In one aspect of the invention the vaccine is capable of providing protection against incident and/or persistent HPV infection by both HPV 31 and 45.

In one aspect of the invention the vaccine does not contain an L1 protein or immunogenic fragment thereof from HPV 31 and 52.

In one aspect of the invention the vaccine is capable of providing protection against incident and for persistent HPV infection by both HPV 31 and 52.

In one aspect of the invention the vaccine of the invention does not contain an L1 protein or immunogenic fragment thereof from HPV 45 and 52.

In one aspect of the invention the vaccine is capable of providing protection against incident and for persistent HPV infection by both HPV 52 and 45.

In one aspect of the invention the vaccine is capable of providing protection against incident and/or persistent HPV infection by HPV 31 and HPV 45 and HPV52.

Suitably the vaccine is capable of protection against persistent infection.

Suitably the vaccine is capable of protection against incident infection.

Incident and persistent cervical infection are defined in Example 1.

We have also determined that a vaccine comprising HPV 16 L1 and HPV 18 L1 proteins (for example, as described in example 1) provides protection against cytological abnormalities caused by certain other oncogenic HPV types such as HPV 52, and is significantly protective with respect to such abnormalities caused by a group of HPV high risk types (defined as 31, 33, 35, 39, 45, 51, 52, 56, 58, 59, 66, and 68). Cytological abnormalities are suitably detected by the well known Pap smear technique.

Thus the invention further relates to use of a combination of an L1 protein or immunogenic fragment thereof from HPV 16 and HPV 18 in the preparation of a composition for the prevention of cytological abnormalities or reduction of the frequency of cytological abnormalities in an individual caused by other (non HPV 16, HPV 18) HPV types, suitably oncogenic HPV types, and in the prevention of histologically-confirmed CIN lesions (CIN 1, CIN 2, CIN 3) and cervical cancer associated with infection by HPV types which are not HPV 16 or 18. Said use is in addition to the prevention or reduction of such events caused by the HPV types in the vaccine, HPV 16 and 18.

Suitably the prevention of cytological abnormalities, reduction of the frequency of cytological abnormalities or prevention of histological-confirmed CIN lesions is prevention against those abnormalities or lesions caused by types not included in the combination, suitably selected from the list of HPV 31, HPV 45 and HPV 52, or is prevention against those abnormalities or lesions caused by the group of 31, 33, 35, 39, 45, 51, 52, 56, 58, 59, 66, and 68. Said use is in addition to the prevention or reduction of such events caused by the HPV types in the vaccine, HPV 16 and 18.

Suitably the composition comprising HPV 16 and HPV 18 for use as above is the multivalent HPV vaccine of the invention, the vaccine comprising an L1 protein or immunogenic fragment thereof from at least 3 different oncogenic HPV types, those types including HPV 16 and HPV 18, wherein the vaccine does not comprise an L1 protein or immunogenic fragment thereof from an HPV type selected from the list consisting of HPV 31, HPV 45, HPV 52 or any combination thereof.

The vaccine of the invention comprises L1 or immunogenic fragment from HPV 16, HPV 18 and at least one other oncogenic HPV type. The oncogenic HPV types are those types associated with a risk of cervical cancer and those oncogenic types that might be included in the vaccine of the invention in addition to HPV 16 and HPV 18 include, but are not limited to, HPV 31, 33, 35, 39, 45, 51, 52, 56, 58, 59, 66 and 68, with the proviso that the vaccine does not comprise all of HPV 31, 45 and 52.

The vaccine of the invention suitably comprises an HPV 33 L1 protein or immunogenic fragment thereof.

The vaccine of the invention suitably comprises an HPV 58 L1 protein or immunogenic fragment thereof.

The vaccine of the invention suitably comprises an HPV 59 L1 protein or immunogenic fragment thereof.

The vaccine of the invention suitably comprises an HPV 16 L1 protein or immunogenic fragment thereof, HPV 18 L1 protein or immunogenic fragment thereof, HPV 33 L1 protein or immunogenic fragment thereof and HPV 58 L1 protein or immunogenic fragment thereof.

L1 proteins or protein fragments from additional HPV types can be included in the vaccine of the invention, such as skin types (in particular HPV 5 and 8) and types associated with genital warts, such as HPV 6 and 11. Types 6 and 11 are not considered oncogenic types herein.

In one aspect of the invention the vaccine may include an HPV early antigen, for example an antigen selected from the list consisting of HPV E1, E2, E3, E4, E5, E6, E7, E8 or E9. In an alternative aspect the vaccine may lack an HPV early antigen, for example an antigen selected from the list consisting of HPV E1, E2, E3, E4, E5, E6, E7, E8 or E9.

In one aspect the vaccine of the invention is trivalent (contains an HPV L1 or fragment thereof from 3 different oncogenic HPV types). In a further aspect the vaccine is tetravalent. In a further aspect the vaccine is pentavalent. In a further aspect the vaccine is heptavalent. In a further aspect the vaccine is septavalent. In a further aspect the vaccine is octavalent. Higher order valancies are also contemplated herein. In further aspects the vaccine is at least tetravalent, pentavalent, heptavalent, septavalent or octavalent with respect to oncogenic HPV types.

Preferably the combination of HPV components within the vaccine does not significantly impact the immunogenicity of any one HPV component. In particular it is preferred that there is no biologically relevant interference between HPV antigens in the combination of the invention, such that the combined vaccine of the invention is able to offer effective protection against infection by each HPV genotype represented in the vaccine. Suitably the immune response against a given HPV type in the combination is at least 50% of the immune response of that same HPV type when measured individually, preferably 100% or substantially 100%. For responses to the HPV 16 and HPV 18, the combined vaccine of the invention preferably stimulates an immune response which is at least 50% of that provided by a combined HPV 16/HPV 18 vaccine. Suitably the immune response generated by the vaccine of the invention is at a level in which the protective effect of each HPV type is still seen. The immune response may suitably be measured, for example, by antibody responses, in either preclinical or human experiments. Measurement of antibody responses is well known in the art, and disclosed in (for example) WO03/077942.

Use of an HPV 16, HPV 18 Vaccine

We have determined that a vaccine comprising HPV 16 L1 and HPV 18 L1 proteins (e.g. see example 1) provides cross protection against infection or disease caused by certain HPV types. As well as providing novel compositions, this information allows new uses to be developed.

In particular, the invention relates to use of a composition comprising HPV 16 and HPV 18 L1 protein, or immunogenic fragment thereof, in the manufacture of a medicament for prevention of infection by HPV 31.

The invention further relates to use of a composition comprising HPV 16 and HPV 18 L1 protein, or immunogenic fragment thereof, in the manufacture of a medicament for prevention of infection by HPV 45.

The invention further relates to use of a composition comprising HPV 16 and HPV 18 L1 protein, or immunogenic fragment thereof in the manufacture of a medicament for prevention of infection by HPV 52.

The composition for said use may lack an antigenic component from the HPV type for which cross protection is provided. Alternatively the composition for said use may comprise such an antigenic component, e.g. the L1 protein or fragment thereof from said cross protected type. In the latter case the use of the composition comprising HPV 16 and HPV 18 L1 protein, or immunogenic fragment thereof, provides both cross protection (e.g. against HPV 31, 45 and 52) and homologous protection (against HPV 16 and HPV 18).

HPV L1 Antigen

Where the vaccine or composition of the invention comprises an immunogenic fragment of L1, then suitable immunogenic fragments of HPV L1 include truncations, deletions, substitution, or insertion mutants of L1. Such immunogenic fragments are suitably capable of raising an immune response (if necessary, when adjuvanted), said immune response being capable of recognising an L1 protein such as a virus like particle, from the HPV type from which the L1 protein was derived.

A suitable immunogenic fragment of HPV 16 is capable of cross protection against at least one of HPV 31 and HPV 52, and in an aspect of the invention, capable of cross protection against both.

A suitable immunogenic fragment of HPV 18 is capable of cross protection against HPV 45.

Cross protection obtainable by immunogenic fragments of HPV 16 and/or HPV 18 can be assessed by trials in humans, for example as outlined in Example 1.

Similarly, different vaccines according to the present invention can be tested using standard techniques, for example as in Example 1, or in standard preclinical models, to confirm that the vaccine is immunogenic.

Suitable immunogenic L1 fragments include truncated L1 proteins. In one aspect the truncation removes a nuclear localisation signal. In another aspect the truncation is a C terminal truncation. In a further aspect the C terminal truncation removes fewer than 50 amino acids, such as fewer than 40 amino acids. Where the L1 is from HPV 16 then in another aspect the C terminal truncation removes 34 amino acids from HPV 16 L1. Where the L1 is from HPV 18 then in a further aspect the C terminal truncation removes 35 amino acids from HPV 18 L1. (Terminated) Truncated L1 Proteins are described in U.S. Pat. No. 6,060,324, U.S. Pat. No. 6,361,778, and U.S. Pat. No. 6,599,508 incorporated herein by reference.

In one aspect the HPV 16 sequence is the following sequence:
(SEQ ID NO: 1)

```
MSLWLPSEATVYLPPVPVSKVVSTDEYVARTNIYYHAGTSRLLAVGHPYFPIKKPNNNKI    60

LVPKVSGLQYRVFRIHLPDPNKFGFPDTSFYNPDTQRLVWACVGVEVGRGQPLGVGISGH   120

PLLNKLDDTENASAYAANAGVDNRECISMDYKQTQLCLIGCKPPIGEHWGKGSPCTNVAV   180

NPGDCPPLELINTVIQDGDMVDTGFGAMDFTTLQANKSEVPLDICTSICKYPDYIKMVSE   240

PYGDSLFFYLRREQMFVRHLFNRAGAVGENVPDDLYIKGSGSTANLASSNYFPTPSGSMV   300

TSDAQIFNKPYWLQRAQGHNNGICWGNQLFVTVVDTTRSTNMSLCAAISTSETTYKNTNF   360

KEYLRHGEEYDLQFIFQLCKITLTADVMTYIHSMNSTILEDWNFGLQPPPGGTLEDTYRF   420

VTSQAIACQKHTPPAPKEDPLKKYTFWEVNLKEKFSADLDQFPLGRKFLLQ            471
```

The HPV 16 sequence may also be that disclosed in WO9405792 or U.S. Pat. No. 6,649,167, for example, suitably truncated. Suitable truncates are truncated at a position equivalent to that shown above, as assessed by sequence comparison.

In one aspect the HPV 18 sequence is the following sequence:

(SEQ ID NO: 2)

```
MALWRPSDNTVYLPPPSVARVVNTDDYVTRTSIFYHAGSSRLLTVGNPYFRVPAGGGNKQ   60

DIPKVSAYQYRVFRVQLPDPNKFGLPDNSIYNPETQRLVWACVGVEIGRGQPLGVGLSGH  120

PFYNKLDDTESSHAATSNVSEDVRDNVSVDYKQTQLCILGCAPAIGEHWAKGTACKSRPL  180

SQGDCPPLELKNTVLEDGDMVDTGYGAMDFSTLQDTKCEVPLDICQSICKYPDYLQMSAD  240

PYGDSMFFCLRREQLFARHFWNRAGTMGDTVPPSLYIKGTGMRASPGSCVYSPSPSGSIV  300

TSDSQLFNKPYWLHKAQGHNNGVCWHNQLFVTVVDTTRSTNLTICASTQSPVPGQYDATK  360

FKQYSRHVEEYDLQFIFQLCTITLTADVMSYIHSMNSSILEDWNFGVPPPPTTSLVDTYR  420

FVQSVAITCQKDAAPAENKDPYDKLKFWNVDLKEKFSLDLDQYPLGRKFLVQ          472
```

An alternative HPV 18 sequence is disclosed in WO9629413, which may be suitably truncated. Suitable truncates are truncated at a position equivalent to that shown above, as assessed by sequence comparison.

Other HPV 16 and HPV 18 sequences are well known in the art and may be suitable for use in the present invention.

Suitable truncations of HPV 31, HPV 45 and HPV 52 may also be made, suitably removing equivalent C terminal portions of the L1 protein to those described above as assessed by sequence alignment.

Truncated L1 proteins are disclosed in, for example, WO9611272 and U.S. Pat. No. 6,066,324, herein incorporated by reference.

The L1 protein or fragment of the invention may optionally be in the form of a fusion protein, such as the fusion of the L1 protein with L2 or an early protein.

The HPV L1 protein is suitably in the form of a capsomer or virus like particle (VLP). In one aspect HPV VLPs may be used in the present invention. HPV VLPs and methods for the production of VLPs are well known in the art. VLPs typically are constructed from the L1 and optionally L2 structural proteins of the virus, see for example WO9420137, U.S. Pat. No. 5,985,610, WO9611272, U.S. Pat. No. 6,599,508B1, U.S. Pat. No. 6,361,778B1, EP 595935 Any suitable HPV VLP may be used in the present invention which provides cross protection, such as an L1 or L1+L2 VLP.

Suitably the VLP is an L1-only VLP.

In one aspect of the invention the vaccine comprises HPV 16 and HPV 18 L1 only VLPs, suitably in combination with an L1 VLP selected from HPV 31, 33, 35, 39, 45, 51, 52, 56, 58, 59, 66 and 68, with the proviso that the vaccine does not comprise VLPs from all of HPV 31, 45 and 52.

VLP formation can be assessed by standard techniques such as, for example, electron microscopy and dynamic laser light scattering.

The VLP may comprise full length L1 protein. In one aspect the L1 protein used to form the VLP is a truncated L1 protein, as described above.

VLPs may be made in any suitable cell substrate such as yeast cells or insect cells e.g. baculovirus cells, and techniques for preparation of VLPs are well known in the art, such as WO9913056, U.S. Pat. No. 6,416,945B1, U.S. Pat. No. 6,261,765B1 and U.S. Pat. No. 6,245,568, and references therein, the entire contents of which are hereby incorporated by reference.

VLPS are suitably made by disassembly and reassembly techniques, which can provide for more stable and/or homogeneous papillomavirus VLPs. For example, McCarthy et al, 1998 "Quantitative Disassembly and Reassembly of Human Papillomavirus Type 11 Virus like Particles in Vitro" J. Virology 72(1):33-41, describes the disassembly and reassembly of recombinant L1 HPV 11 VLPs purified from insect cells in order to obtain a homogeneous preparation of VLP's. WO9913056 and U.S. Pat. No. 6,245,568 also describe disassembly/reassembly processes for making HPV VLPs.

In one aspect HPV VLPS are made as described WO9913056 or U.S. Pat. No. 6,245,568.

Optional Vaccine Components

The HPV L1 the invention may be combined with an adjuvant or immunostimulant such as, but not limited to, detoxified lipid A from any source and non-toxic derivatives of lipid A, saponins and other reagents capable of stimulating a TH1 type response.

It has long been known that enterobacterial lipopolysaccharide (LPS) is a potent stimulator of the immune system, although its use in adjuvants has been curtailed by its toxic effects. A non-toxic derivative of LPS, monophosphoryl lipid A (MPL), produced by removal of the core carbohydrate group and the phosphate from the reducing-end glucosamine, has been described by Ribi et al (1986, Immunology and Immunopharmacology of bacterial endotoxins, Plenum Publ. Corp., NY, p 407-419) and has the following structure:

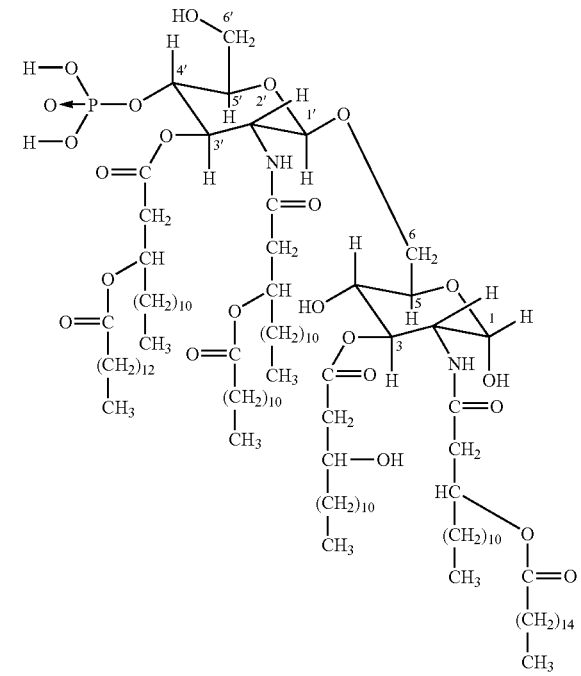

A further detoxified version of MPL results from the removal of the acyl chain from the 3-position of the disaccharide backbone, and is called 3-O-Deacylated monophosphoryl lipid A (3D-MPL). It can be purified and prepared by the methods taught in GB 2122204B, which reference also discloses the preparation of diphosphoryl lipid A, and 3-O-deacylated variants thereof.

A suitable form of 3D-MPL is in the form of an emulsion having a small particle size less than 0.2 µm in diameter, and its method of manufacture is disclosed in WO 94/21292. Aqueous formulations comprising monophosphoryl lipid A and a surfactant have been described in WO9843670A2.

The bacterial lipopolysaccharide derived adjuvants to be formulated in the compositions of the present invention may be purified and processed from bacterial sources, or alternatively they may be synthetic. For example, purified monophosphoryl lipid A is described in Ribi et al 1986 (supra), and 3-O-Deacylated monophosphoryl or diphosphoryl lipid A derived from *Salmonella* sp. is described in GB 2220211 and U.S. Pat. No. 4,912,094. Other purified and synthetic lipopolysaccharides have been described (Hilgers et al., 1986, *Int. Arch. Allergy. Immunol.*, 79(4):392-6; Hilgers et al., 1987, Immunology, 60(1):141-6; and EP 0 549 074 B1). In one aspect the bacterial lipopolysaccharide adjuvant is 3D-MPL.

Accordingly, the LPS derivatives that may be used in the present invention are those immunostimulants that are similar in structure to that of LPS or MPL or 3D-MPL. In another aspect of the present invention the LPS derivatives may be an acylated monosaccharide, which is a sub-portion to the above structure of MPL.

Saponins are taught in: Lacaille-Dubois, M and Wagner H. (1996. A review of the biological and pharmacological activities of saponins. Phytomedicine vol 2 pp 363-386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Haemolysis of erythrocytes is an example of this phenomenon, which is a property of certain, but not all, saponins.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree Quillaja Saponaria Molina), and fractions thereof, are described in U.S. Pat. No. 5,057,540 and "Saponins as vaccine adjuvants", Kensil, C. R., *Crit Rev Ther Drug Carrier Syst*, 1996, 12 (1-2):1-55; and EP 0 362 279 B1. Particulate structures, termed Immune Stimulating Complexes (ISCOMS), comprising fractions of Quil A are haemolytic and have been used in the manufacture of vaccines (Morein, B., EP 0 109 942 B1; WO 96/11711; WO 96/33739). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Other saponins which have been used in systemic vaccination studies include those derived from other plant species such as *Gypsophila* and *Saponaria* (Bomford et al., Vaccine, 10(9):572-577, 1992).

An enhanced system involves the combination of a non-toxic lipid A derivative and a saponin derivative particularly the combination of QS21 and 3D-MPL as disclosed in WO 94/00153, or a less reactogenic composition where the QS21 is quenched with cholesterol as disclosed in WO 96/33739.

A particularly potent adjuvant formulation involving QS21 and 3D-MPL in an oil in water emulsion is described in WO 95/17210 and use of this adjuvant forms an aspect of the invention.

Accordingly in one embodiment of the present invention there is provided a vaccine adjuvanted with detoxified lipid A or a non-toxic derivative of lipid A, more suitably adjuvanted with a monophosphoryl lipid A or derivative thereof.

In one aspect the vaccine additionally comprises a saponin, for example QS21.

In one aspect the formulation additionally comprises an oil in water emulsion. The present invention also provides a method for producing a vaccine formulation comprising mixing an L2 peptide of the present invention together with a pharmaceutically acceptable excipient, such as 3D-MPL.

Additional components that may be included present in an vaccine formulation according to the invention include non-ionic detergents such as the octoxynols and polyoxyethylene esters as described herein, particularly t-octylphenoxy polyethoxyethanol (Triton X-100) and polyoxyethylene sorbitan monooleate (Tween 80); and bile salts or cholic acid derivatives as described herein, in particular sodium deoxycholate or taurodeoxycholate. Thus, in one aspect of the invention a formulation comprises 3D-MPL, Triton X-100, Tween 80 and sodium deoxycholate, which may be combined with an L2 antigen preparation to provide a suitable vaccine.

In one embodiment of the present invention, the vaccine comprises a vesicular adjuvant formulation comprising cholesterol, a saponin and an LPS derivative. In this regard the adjuvant formulation suitably comprises a unilamellar vesicle comprising cholesterol, having a lipid bilayer suitably comprising dioleoyl phosphatidyl choline, wherein the saponin and the LPS derivative are associated with, or embedded within, the lipid bilayer. In one aspect these adjuvant formulations comprise QS21 as the saponin, and 3D-MPL as the LPS derivative, wherein the ratio of QS21:cholesterol is from 1:1 to 1:100 weight/weight, and in one aspect, a ratio of 1:5 weight/weight. Such adjuvant formulations are described in EP 0 822 831 B, the disclosure of which is incorporated herein by reference.

Suitably the vaccines of the invention are used in combination with aluminium, and are suitably adsorbed or partially adsorbed onto aluminium adjuvants. Suitably the adjuvant is an aluminium salt, which may be in combination with 3D MPL, such as aluminium phosphate and 3D MPL. Aluminium hydroxide, optionally in combination with 3D MPL is also suitable.

In another aspect of the present invention the vaccine comprises the combination of HPV VLPs with an aluminium salt or with an aluminium salt +3D MPL. Aluminium hydroxide is suitable as the aluminium salt.

The vaccine may also comprise aluminium or an aluminium compound as a stabiliser.

The vaccines of the invention may be provided by any of a variety of routes such as oral delivery (e.g. see WO9961052 A2), topical, subcutaneous, mucosal (typically intravaginal), intravenous, intramuscular, intranasal, sublingual, intradermal and via suppository.

Optionally the vaccine may also be formulated or co-administered with other HPV antigens or non-HPV antigens. Suitably these non-HPV antigens can provide protection against other diseases, such as sexually transmitted diseases such as herpes simplex virus, EBV, chlamydia and HIV. We particularly prefer that the vaccine comprises gD or a truncate thereof from HSV. In this way the vaccine provides protection against both HPV and HSV.

The dosage of the vaccine components will vary with the condition, sex, age and weight of the individual, the administration route and HPV of the vaccine. The quantity may also be varied with the number of VLP types. Suitably the delivery is of an amount of vaccine suitable to generate an immunologically protective response. Suitably each vaccine dose comprises 1-100 µg of each VLP, in one aspect 5-80 µg, in another aspect 5-30 µg each VLP, in a further aspect 5-20 µg of each VLP, in a yet further aspect 5 µg, 6 µg, 10 µg, 15 µg or 20 µg.

For all vaccines of the invention, in one aspect the vaccine is used for the vaccination of adolescent girls aged 10-15, such as 10-13 years. However, older girls above 15 years old and adult women may also be vaccinated. The vaccine may also be administered to women following an abnormal pap smear or after surgery following removal of a lesion caused by HPV, or who are seronegative and DNA negative for HPV cancer types.

In one aspect the vaccine is delivered in a 2 or 3 dose regime, for example in a 0, 1 month regime or 0, 1 and 6 month regime respectively. Suitably the vaccination regime incorporates a booster injection after 5 to 10 years, such as 10 years.

In one aspect the vaccine is a liquid vaccine formulation, although the vaccine may be lyophilised and reconstituted prior to administration.

The teaching of all references in the present application, including patent applications and granted patents, are herein fully incorporated by reference.

The vaccines of the invention comprise certain HPV components as laid out above. In a further aspect of the invention the vaccine consists essentially of, or consists of, said components.

The term 'vaccine', as used in the present invention, refers to a composition that comprises an immunogenic component capable of provoking an immune response in an individual, such as a human, optionally when suitably formulated or adjuvant.

The present invention is now described with respect to the following examples which serve to illustrate the invention.

Example 1

Precise details of the experiment carried out are provided in Harper et al, the Lancet. 2004 Nov. 13; 364(9447):1757-65, incorporated herein by reference.

In summary, healthy women between the ages of 15 and 25 years were immunised with a mixture of HPV 16 and HPV 18 L1 VLPs. The women at enrolment were: 1) seronegative for HPV-16 and HPV-18; 2) negative for high risk HPV infection of the cervix (detected by HPV PCR); 3) had 6 or fewer lifetime sexual partners and 4) had normal PAP smears.

The mixture comprised, per 0.5 ml dose, 20 µg of HPV-16 L1 VLP, 20 µg of HPV-18 L1 VLP and was adjuvanted with 500 µg of aluminum hydroxide and 50 µg of 3D MPL. The placebo group was injected with 500 µg of aluminum hydroxide alone.

The vaccine efficacy (V.E.) against certain cancer HPV types was assessed, wherein the V.E. is the % improvement in protection against infection by the vaccine compared to a placebo group.

Cross protection was assessed by detecting the presence of nucleic acid specific for various oncogenic types in the vaccinees and control group. Detection was carried out using techniques as described in WO03014402, and references therein, particularly for non-specific amplification of HPV DNA and subsequent detection of DNA types using a LiPA system as described in WO 99/14377, and in Kleter et al, [Journal of Clinical Microbiology (1999), 37 (8): 2508-2517], the whole contents of which are herein specifically incorporated by reference.

Any suitable method can, however, be used for the detection of HPV DNA in a sample, such as type specific PCR using primers specific for each HPV type of interest. Suitable primers are known to the skilled person, or can be easily constructed given that the sequences of the oncogenic HPV types are known.

In Detail, the Methods Section of the Lancet Paper is Reproduced Here, for Completeness:

The primary objective of this study was to assess vaccine efficacy in the prevention of infection with HPV-16, HPV-18, or both (HPV-16/18), between months 6 and 18 in participants who were initially shown to be seronegative for HPV-16/18 by ELISA and negative for RPV-16/18 DNA by PCR. Secondary objectives included: evaluation of vaccine efficacy in the prevention of persistent infection with HPV-16/18, and the evaluation of vaccine efficacy in the prevention of cytologically confirmed low-grade squamous intraepithelial lesions (LSIL), high-grade squamous intraepithelial lesions (HSIL), and histologically confirmed LSIL (CIN 1), HSIL (CIN 2 or 3) squamous cell cancer, or adenocarcinoma associated with HPV-16/18 infection between months 6 and 18, and months 6 and 27. The prevention of atypical squamous cells of undetermined significance (ASCUS) cytology associated with HPV-16/18 infection was added post-hoc to the outcome analyses.

We also did an exploratory analysis of the histopathological endpoints CIN 1 and 2 associated with HPV-16/18 DNA detected by PCR in lesional tissue. Other objectives included the assessment of vaccine immunogenicity, safety, and tolerability. Investigators in North America (Canada and the USA) and Brazil recruited women for this efficacy study through advertisements or previous participation in an HPV cross-sectional epidemiology study that took place between July and December, 2000. For each of the 32 study sites, an institutional review board approved the protocol, consent forms, and amendments. Women signed separate written consents for study participation and colposcopy. For those under 18 years, parental consent and assent from the participant were obligatory.

There were two study phases: an initial phase for vaccination and follow-up that concluded at month 18; and a blinded follow-up extension phase that concluded at month 27.

Women eligible for the initial phase (months 0-18) included healthy women aged 15-25 years, who had had no more than six sexual partners, no history of an abnormal Pap test or ablative or excisional treatment of the cervix, and no ongoing treatment for external condylomata; and who were cytologically negative, seronegative for HPV-16 and HPV-18 antibodies by ELISA, and HPV-DNA-negative by PCR for 14 high-risk HPV types (16, 18, 31, 33, 35, 39, 45, 51, 52, 56, 58, 59, 66, and 68) no more than 90 days before study entry.

Women who completed the initial phase of the study earliest, and who did not have ablative or excisional therapy of the cervix, or hysterectomy after enrolment, were eligible to participate in the extension phase of the study (months 18-27).

Procedures

Each dose of the bivalent HPV-16/18 virus-like particle vaccine (GlaxoSmithKline Biologicals, Rixensart, Belgium) contained 20 μg of HPV-16 L1 virus-like particle and 20 μg of HPV-18 L1 virus-like particle. Each type of virus-like particle was produced on *Spodoptera frugiperda* Sf-9 and *Trichoplusia ni* Hi-5 cell substrate with AS04 adjuvant containing 500 μg aluminum hydroxide and 50 μg 3-deacylated monophosphoryl lipid A (MPL, Corixa, Mont., USA) provided in a monodose vial. The placebo contained 500 μg of aluminum hydroxide per dose, and was identical in appearance to the HPV-16/18 vaccine. Every study participant received a 0.5 mL dose of vaccine or placebo at 0 months, 1 month, and 6 months. Health-care providers obtained cervical specimens with a cervical brush and spatula (washed in PreservCyt, Cytyc Corporation, Boxborough, Mass., USA) for cytology and HPV DNA testing at screening and months 6, 12, and 18. At months 0 and 6, and subsequently every 3 months, women self-obtained cervicovaginal samples with two sequential swabs (placed in PreservCyt) for HPV DNA testing. [D M Harper, W W Noll, D R Belloni and B F. Cole, Randomized clinical trial of PCR-determined human papillomavirus detection methods: self-sampling versus clinician-directed—biologic concordance and women's preferences. *Am J Obstet Gynecol* 186 (2002), pp. 365-373] A central laboratory (Quest Diagnostics, Teterboro, N.J., USA) reported cytology results (ThinPrep, Cytyc Corporation) by use of the 1991 Bethesda classification system. Protocol guidelines recommended colposcopy after two reports of ASCUS, or one report of atypical glandular cells of undetermined significance, LSIL or HSIL, squamous cell carcinoma, adenocarcinoma in situ, or adenocarcinoma. These guidelines also recommended biopsy for any suspected lesions.

The central histology laboratory made an initial diagnosis from the formalin-fixed tissue specimens for clinical management. A panel of three pathologists made a subsequent consensus diagnosis for HPV-16 and HPV-18 associated lesions with the CIN system. This consensus diagnosis also included review of the sections taken at the time of microdissection for PCR detection of lesional HPV DNA.

HPV DNA isolated from the cytology specimen (MagNaPure Total Nucleic Acid system, Roche Diagnostics, Almere, Netherlands) and from the cervical biopsy specimen (proteinase K extraction) was amplified from an aliquot of purified total DNA with the SPF10 broad-spectrum primers that amplify a 65 by region of the L1 gene. [B Kleter, L J van Doom, J ter Schegget et al., Novel short-fragment PCR assay for highly sensitive broad-spectrum detection of anogenital human papillomaviruses. *Am J Pathol* 153 (1998), pp. 1731-1739: L J van Doom, W Quint, B Kleter et al., Genotyping of human papillomavirus in liquid cytology cervical specimens by the PGMY line blot assay and the SPF(10) line probe assay. *J Clin Microbiol* 40 (2002), pp. 979-983 and W G Quint, G Scholte, L J van Doom, B Kleter, P H Smits and J. Lindeman, Comparative analysis of human papillomavirus infections in cervical scrapes and biopsy specimens by general SPF(10) PCR and HPV genotyping. *J Pathol* 194 (2001), pp. 51-58] The amplification products were detected by a DNA enzyme immunoassay. A line probe assay (LiPA Kit HPV INNO LiPA HPV genotyping assay, SPF-10 system version 1, Innogenetics, Gent, Belgium, manufactured by Labo Bio-medical Products, Rijswijk, Netherlands) detected 25 HPV genotypes (6, 11, 16, 18, 31, 33, 34, 35, 39, 40, 42, 43, 44, 45, 51, 52, 53, 56, 58, 59, 66, 68, 70, and 74). [B Kleter, L J van Doom, L Schrauwen et al., Development and clinical evaluation of a highly sensitive PCR-reverse hybridization line probe assay for detection and identification of anogenital human papillomavirus. *J Clin Microbiol* 37 (1999), pp. 2508-2517] Any specimen that was positive by DNA enzyme immunoassay was tested by type-specific HPV-16 and HPV-18 PCR. HPV-16 type-specific PCR primers amplified a 92 by segment of the E6/E7 gene and HPV-18 type-specific PCR primers amplified a 126 by segment of the L1 gene. [M F Baay, W G Quint, J Koudstaal et al., Comprehensive study of several general and type-specific primer pairs for detection of human papillomavirus DNA by PCR in paraffin-embedded cervical carcinomas. *J Clin Microbiol* 34 (1996), pp. 745-747]

We defined incident cervical infection with HPV-16/18 as at least one positive PCR result for HPV-16 or HPV-18 during the trial, and persistent infection with HPV-16/18 as at least two positive HPV-DNA PCR assays for the same viral genotype separated by at least 6 months. [H Richardson, G Kelsall, P Tellier et al., The natural history of type-specific human papillomavirus infections in female university students. *Cancer Epidemiol Biomarkers Prev* 12 (2003), pp. 485-490 and A B Moscicki, J H Ellenberg, S Farhat and J. Xu, Persistence of human papillomavirus infection in HIV-infected and -uninfected adolescent girls: risk factors and differences, by phylogenetic type. *J Infect Dis* 190 (2004), pp. 37-45] HPV-DNA test results were concealed from investigators during the study and cytological and histological diagnoses were only revealed for clinical management purposes. Analyses included HPV-16/18 DNA results for cervical specimens and combined cervical and self-obtained cervicovaginal specimens.

We collected serum from study participants at months 0, 1, 6, 7, 12, and 18 for assessment of immunogenicity. Serological testing for antibodies to HPV-16 and HPV-18 virus-like particles was by ELISA. Recombinant HPV-16 or HPV-18 virus-like particles were used as coating antigens for antibody detection (see webappendix http://image.thelancet.com/extras/04art10103webappendix.pdf). Seropositivity was defined as a titre greater than or equal to the assay cut-off titre established at 8 ELISA units/mL for HPV-16 and 7 ELISA units/mL for HPV-18. Typical natural titres were determined by use of blood samples obtained from women in the preceding epidemiology study who were found to be seropositive for HPV-16 or HPV-18 by ELISA.

Women recorded symptoms experienced during the first 7 days after vaccination on diary cards with a three-grade scale of symptom intensity. Additionally, they reported to study personnel by interview all adverse events within the first 30 days after vaccination. Information on serious adverse events and pregnancies was collected throughout the study.

Statistical Methods

Assuming a 6% cumulative incidence rate of both HPV-16 and HPV-18 type infections over 12 months, we estimated that 500 women per treatment group would provide 80% power to assess a lower limit of the 95% CI of the vaccine efficacy above zero. We assumed an 80% retention rate over 18 months. Interim analyses for efficacy, safety, and immunogenicity were done for future study planning purposes only; the O'Brien and Fleming method was used to adjust the α value for the final analysis after interim analyses occurred (overall α=0.05; two-sided test). [PC O'Brien and T R. Fleming, A multiple testing procedure for clinical trials. *Biometrics* 35 (1979), pp. 549-556]

Stratified, block randomisation according to validated algorithms was centralised with an internet randomisation system. Stratification was according to age (15-17, 18-21, and 22-25 years) and region (North America and Brazil). Each vaccine dose was attributed a randomly chosen number based on specific participant information entered into the computerised randomisation system by study personnel. Treatment allocation remains concealed from investigators and the women participating in a long-term follow-up study.

The intention-to-treat and according-to-protocol cohorts are shown in the figure, in which the reasons for exclusion from analyses are listed in rank order; women who met more than one exclusion criterion were only counted once according to the highest ranking criterion. We refer to the sets of participants entered in the intention-to-treat and according-to-protocol analyses as cohorts, although the information used to restrict subject inclusion in the according-to-protocol was only known after follow-up. We did both according-to-protocol and intention-to-treat analyses for efficacy. Calculation of vaccine efficacy in the according-to-protocol 18-month analysis was based on the proportion of participants with HPV-16/18 infection in the vaccinated versus placebo groups. Vaccine efficacy was defined as 1 minus the ratio between these two proportions; 95% CIs measured the precision of the efficacy estimates. p values were calculated with the two-sided Fisher's exact test. Corresponding rates were expressed as the numbers of cases with the outcome divided by the numbers of participants at risk. The according-to-protocol 18-month cohort included enrolled women who received three scheduled doses of vaccine and complied with the protocol as described in the figure.

Calculation of vaccine efficacy in the intention-to-treat and according-to-protocol 27-month analyses was based on the Cox proportional hazard model using the time-to-occurrence of cases with HPV-16/18 infection in the vaccinated versus placebo groups. This allowed controlling for the accrued person-time data in each group. Vaccine efficacy was calculated using 1 minus the hazard ratio and p values calculated using the log rank test. Corresponding rates were expressed as the number of cases divided by the total person-time. All enrolled women who received at least one dose of vaccine or placebo, were negative for high-risk HPV-DNA at month 0, and had any data available for outcome measurement were included in the intention-to-treat cohort.

The according-to-protocol 27-month cohort included outcome results from the according-to-protocol 18-month cohort and results that occurred during the extension phase (from 18 months to 27 months).

Figure 1B:
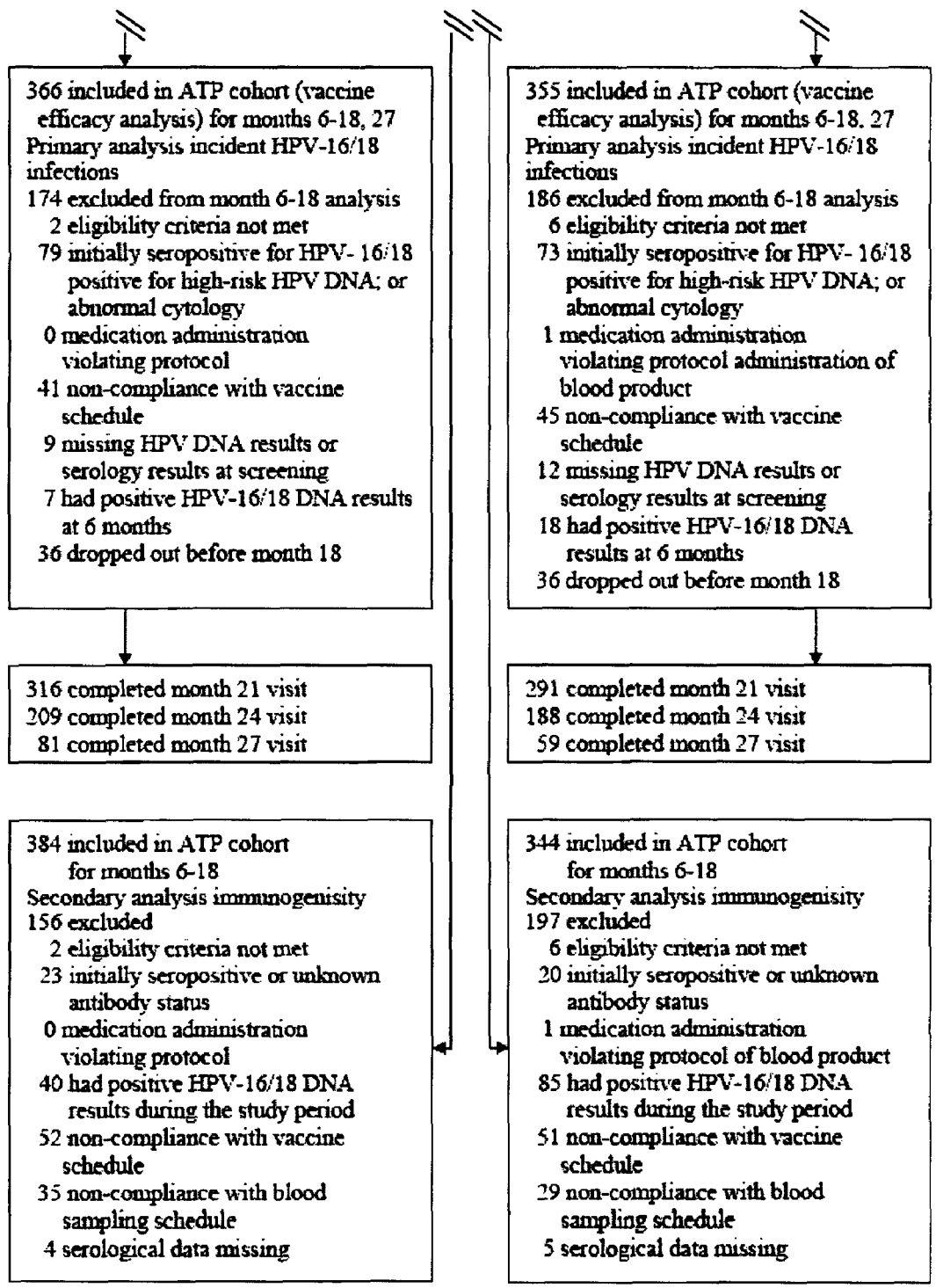

Calculation of p values for the safety analysis was performed using Fisher's exact test comparisons. The cohort for safety analysis included all enrolled women who received at least one dose of vaccine or placebo and complied with specified, minimal protocol requirements (see FIG. 1).

Immunogenicity was assessed in a subset of the according-to-protocol safety cohort, which included women with serology results at months 0, 7, and 18, who received all three doses of study vaccine or placebo according to schedule, complied with the blood sampling schedule, and did not become positive for HPV-16/18-DNA during the trial. Seropositivity rates between the vaccine and placebo groups were compared with Fisher's exact test (p<0.001 judged significant). Geometric mean titres were compared with ANOVA and Kruskal-Wallis test.

Block randomisation and statistical analyses were done with SAS version 8.2 (SAS Institute, Cary, N.C.).

Initial Analysis and Results

Results of the initial analysis on cross protection are presented in patent application WO2004/056389, the whole contents of which herein incorporated by reference.

An initial analysis was carried out on an "ITT" (Intention To Treat cohort, representing all individuals who received at least one dose of vaccine). This data is shown in Table A.

The results presented in Tables B and C relate to the "ATP" (According To Protocol) group for those patients who complied with all the criteria of the trial. Table B is a midpoint analysis with data taken from all patients at the timepoint at which at least 50% of the cohort were 18 months after their first vaccination. Table C gives the final results, all data being from subjects at 18 months post first vaccination (month 0). In the ATP group all patients received 3 doses of vaccine at 0, 1 and 6 months and were seronegative at 6 months.

As demonstrated by the data presented in table A, immunization with a mixture of HPV 16 and HPV 18 VLPs provided apparent cross-protection against other HPV types. At this point the sample sizes are too small to provide for a rigorous statistical analysis, however the data demonstrate a positive trend and suggest that immunization with HPV16 and HPV18 VLPs will be efficacious against infection with other HPV types.

This was confirmed as the study progressed.

Table B demonstrates that HPV 16 and HPV 18 provide statistically significant cross protection against the group of high risk cancer types 31, 33, 35, 39, 45, 51, 52, 56, 58, 59, 66 and 68.

Table C demonstrates that, except for the HPV-18 related types (which show a very strong trend), there is statistically significant cross-protection against the groups of: HPV 31, 35, 58; HPV 31, 33, 35, 52, 58; and the 12 high risk (non HPV-16/18) types evaluated.

Further analysis was carried out on the specific cross protection against specific types.

Vaccine efficacy was assessed against infections and diseases related to the 12 high risk cancer types 31, 33, 35, 39, 45, 51, 52, 56, 58, 59, 66 and 68, HPV-16 phylogenetic-related types (the groups of 31, 35, and 58; 31, 33, 35, 52 and 58) and HPV-18 phylogenetic related types (45 and 59).

An analysis was carried out on an "ATP" (According To Protocol) group for those patients who complied with all the criteria of the trial. In the ATP group all patients received 3 doses of vaccine at 0, 1 and 6 months and were seronegative at 6 months.

As demonstrated by the data presented in Table D, immunization with a mixture of HPV 16 and HPV 18 VLPs provided statistically significant cross protection against incident infection by HPV types 31, 52 and 45 compared to the control.

Statistically significant cross protection against incident infection was also observed against the group of all HPV 16 related types (HPV-31, 33, 35, 52 and 58) and the group of all high risk types, excluding 16 and 18 (HPV 31, 33, 35, 39, 45, 51, 52, 56, 58, 59, 66, and 68).

Statistically significant cross protection against persistent infection was also observed against types 31 and 52 and was also observed against the group of all HPV 16 related types (see Table E).

Statistically significant cross protection was observed against cytological abnormalities associated with HPV 52 and was also observed against cytological abnormalities associated with the group of all HPV 16 related types (HPV-31, 33, 35, 52, and 58) and the group of all high risk types, excluding 16 and 18 (31, 33, 35, 39, 45, 51, 52, 56, 58, 59, 66, and 68) (Table F).

TABLE A

| | HPV types analysed | | | |
|---|---|---|---|---|
| | HPV 31, 35, 58 | HPV 31, 33, 35, 52, 58 | HPV 45, 59 | HPV 31, 33, 35, 39, 45, 51, 52, 56, 58, 59, 66, 68. |
| Number of women infected (vaccine group) | 5 | 17 | 3 | 27 |
| % women infected (vaccine group) = A | 1.1 | 3.8 | 0.7 | 6.3 |
| Number of women infected (placebo group) | 11 | 24 | 6 | 40 |
| % women infected (placebo group) = B | 2.4 | 5.4 | 1.3 | 9.4 |
| % vaccine efficacy $1 - (A/B) \times 100$, adjusted for relative size of vaccine and placebo group | 55.1 | 30.3 | 50.6 | 34.6 |
| 95% confidence limits lower limit | −29.1 | −29.7 | −97.7 | −6.5 |
| 95% confidence limits upper limit | 84.4 | 62.6 | 87.6 | 59.9 |
| P | 0.127 | 0.252 | 0.309 | 0.086 |

Samples were taken at 9, 12, 15, and 18 months from patients and tested for HPV infection by the types specified above.

TABLE B vaccine efficacy after three doses in preventing incident heterologous infections. Table 2: Vaccine efficacy against infection with HPV-16 phylogenetically related types, HPV-18 phylogenetically related types, HPV-16 and/or HPV-18 phylogenetically related types and all high-risk types exclusive of HPV-16 and HPV-18 - ATP cohort (month 6-18)

| | Attack rate | | | | | | Vaccine efficacy | | | |
|---|---|---|---|---|---|---|---|---|---|---|
| | Vaccine | | | Placebo | | | | | | |
| Infection Type | N | n | AR | N | n | AR | % | 95% CI | | p-value |
| HPV-16 related | 433 | 12 | 2.8 | 438 | 24 | 5.5 | 49.4 | 0.2 | 74.4 | 0.060 |
| HPV-16 related* | 423 | 29 | 6.9 | 423 | 46 | 10.9 | 37.0 | 1.6 | 59.6 | 0.052 |
| HPV-18 related | 442 | 9 | 2.0 | 449 | 16 | 3.6 | 42.9 | −27.9 | 74.5 | 0.223 |
| HPV-16/18 related | 433 | 21 | 4.9 | 438 | 41 | 9.4 | 48.2 | 13.8 | 68.9 | 0.012 |
| HPV-16/18 related* | 423 | 34 | 8.0 | 423 | 56 | 13.2 | 39.3 | 9.0 | 59.5 | 0.019 |
| High-risk** | 385 | 53 | 13.8 | 386 | 88 | 22.8 | 39.6 | 17.7 | 55.7 | 0.001 |

N = number of subjects in specific cohort
n = number of subjects with incident HPV infection
AR = Attack rate = n/N
95% CI = 95% confidence interval
lower limit = $1 - \exp(\log(arv/arp) + 1.96 * \sqrt{(1/nv - 1/Nv + 1/np - 1/Np)})$
upper limit = $1 - \exp(\log(arv/arp) - 1.96 * \sqrt{(1/nv - 1/Nv + 1/np - 1/Np)})$
when number of cases in vaccine = 0:
lower limit* = $1 - \exp(\log(arv*/arp*) + 1.96 * \sqrt{(1/(nv + 0.5) - 1/(Nv + 0.5) + 1/(np + 0.5) - 1/(Np + 0.5))})$
upper limit* = $1 - \exp(\log(arv*/arp*) - 1.96 * \sqrt{(1/(nv + 0.5) - 1/(Nv + 0.5) + 1/(np + 0.5) - 1/(Np + 0.5))})$
with:
arv = attack rate in vaccine recipients
arp = attack rate in placebo recipients
nv = number of cases in vaccine recipients
Nv = number of cases and non-cases in vaccine recipients
np = number of cases in placebo recipients
Np = number of cases and non-cases in placebo recipients
HPV-16 related: HPV-16 phylogenetically related types 35, 31, 58 without considering other HPV types
HPV-16 related*: HPV-16 phylogenetically related types 35, 31, 58, 33, 52 without considering other HPV types
HPV-18 related: HPV-18 phylogenetically related types 45, 59 without considering other HPV types
HPV-16 and/or HPV-18 related: HPV-16 and/or HPV-18 phylogenetically related types 35, 31, 58, 45, 59 without considering other HPV types
HPV-16 and/or HPV-18 related*: HPV-16 and/or HPV-18 phylogenetically related types 35, 31, 58, 33, 52, 45, 59 without considering other HPV types
**= High-risk types exclusive of HPV-16 and HPV-18

TABLE C

| | HPV types analysed | | | |
|---|---|---|---|---|
| | HPV 31, 35, 58 | HPV 31, 33, 35, 52, 58 | HPV 45, 59 | HPV 31, 33, 35, 39, 45, 51, 52, 56, 58, 59, 66, 68. |
| Total number of number of subjects with information available per group | 412 | 403 | 421 | 368 |
| Number of women infected (vaccine group) | 11 | 28 | 10 | 58 |
| % women infected (vaccine group) = A | 2.7 | 6.9 | 2.4 | 15.8 |
| Number of women infected (placebo group). | 26 | 48 | 15 | 90 |
| % women infected (placebo group) = B | 6.3 | 12.2 | 3.6 | 25.3 |
| % vaccine efficacy 1 − (A/B) × 100, adjusted for relative size of vaccine and placebo group | 57.9 | 43.0 | 33.5 | 37.7 |
| 95% confidence limits lower limit | 15.9 | 11.0 | −46.3 | 16.2 |
| 95% confidence limits upper limit | 78.9 | 63.5 | 69.8 | 53.6 |
| P | 0.012 | 0.015 | 0.319 | 0.002 |

Samples were taken at 18 months from patients and tested for HPV infection by the types specified above.

TABLE D

Efficacy against Incident Infections with 16/18 Related Types*

| | | Vaccine | | Control | | Vaccine Efficacy | |
|---|---|---|---|---|---|---|---|
| | HPV Type | N | AR | N | AR | % | P value |
| 16 related | HPV-31 | 1 | 0.2 | 10 | 2.4 | 90.0 | 0.006 |
| | HPV-33 | 6 | 1.4 | 6 | 1.4 | −0.2 | 1.000 |
| | HPV-35 | 1 | 0.2 | 3 | 0.7 | 66.5 | 0.624 |
| | HPV-52 | 6 | 1.4 | 16 | 3.9 | 63.0 | 0.031 |
| | HPV-58 | 5 | 1.2 | 5 | 1.2 | 0.0 | 1.000 |
| 18 related | HPV-45 | 0 | 0.0 | 5 | 1.2 | 100.0 | 0.031 |
| | HPV-59 | 4 | 0.9 | 2 | 0.5 | −100.5 | 0.448 |
| | 16 related | 16 | 4.0 | 32 | 8.1 | 51.1 | 0.017 |
| | 18 related | 4 | 1.0 | 7 | 1.7 | 43.0 | 0.384 |
| | 12 HR types** (except 16/18) | 32 | 9.0 | 53 | 15.6 | 42.3 | 0.011 |

*ATP cohort (cervical samples)

TABLE E

Efficacy against Persistent Infections with 16/18 Related Types*

| | | Vaccine | | Control | | Vaccine Efficacy | |
|---|---|---|---|---|---|---|---|
| | HPV Type | N | AR | N | AR | % | P value |
| 16 related | HPV-31 | 2 | 0.48 | 9 | 2.15 | 78.5 | 0.030 |
| | HPV-33 | 3 | 0.71 | 5 | 1.18 | 40.2 | 0.476 |
| | HPV-35 | 1 | 0.24 | 1 | 0.24 | 0.4 | 0.998 |
| | HPV-52 | 5 | 1.20 | 21 | 5.10 | 77.1 | 0.001 |
| | HPV-58 | 4 | 0.95 | 6 | 1.42 | 34.1 | 0.515 |
| 18 related | HPV-45 | 1 | 0.24 | 4 | 0.94 | 75.4 | 0.174 |
| | HPV-59 | 3 | 0.71 | 0 | 0.00 | — | 0.083 |
| | 16 related | 11 | 2.7 | 30 | 7.6 | 65.1 | 0.002 |
| | 18 related | 4 | 1.0 | 4 | 1.0 | 1.0 | 0.989 |

TABLE E-continued

Efficacy against Persistent Infections with 16/18 Related Types*

| | Vaccine | | Control | | Vaccine Efficacy | |
|---|---|---|---|---|---|---|
| HPV Type | N | AR | N | AR | % | P value |
| 12 HR types (except 16/18) | 36 | 10.1 | 46 | 13.5 | 27.1 | 0.155 |

*ATP cohort (all samples)

TABLE F

Efficacy against Cytological Abnormalities due to Related Types*

| | | Vaccine | | Control | | Vaccine Efficacy | |
|---|---|---|---|---|---|---|---|
| | HPV Type | N | AR | N | AR | % | P value |
| 16 related | HPV-31 | 1 | 0.24 | 5 | 1.20 | 80.1 | 0.123 |
| | HPV-33 | 2 | 0.47 | 4 | 0.94 | 49.9 | 0.686 |
| | HPV-35 | 0 | 0.00 | 2 | 0.47 | 100 | 0.499 |
| | HPV-52 | 1 | 0.24 | 11 | 2.67 | 91 | 0.003 |
| | HPV-58 | 2 | 0.47 | 2 | 0.47 | 0.2 | 1.000 |
| 18 related | HPV-45 | 0 | 0.00 | 2 | 0.47 | 100 | 0.249 |
| | HPV-59 | 4 | 0.94 | 2 | 0.47 | −101 | 0.451 |
| | 16 related | 5 | 1.2 | 18 | 4.6 | 72.8 | 0.005 |
| | 18 related | 4 | 1.0 | 4 | 1.0 | 0.2 | 1.000 |
| | 12 HR types (except 16/18) | 10 | 2.8 | 30 | 8.8 | 68.2 | <0.001 |

*ATP cohort

In tables D, E and F,

N=number of subjects in specific cohort

AR=Attack rate=n (number of subjects with HPV either incident infection, persistent infection or cytological abnormality, as appropriate for the table)/N % Vaccine efficacy is 1−(A/B)×100, adjusted for relative size of vaccine and placebo group, wherein A=% women in vaccine group with incident infection, persistent infection or cytological abnormality, as appropriate for the table B=% women in placebo group with incident infection, persistent infection or cytological abnormality, as appropriate for the table

What is claimed is:

1. A multivalent HPV vaccine comprising L1 proteins or immunogenic fragments thereof from HPV 16, HPV 18 and at least one other oncogenic HPV type, which at least one other oncogenic HPV type is HPV 33, HPV59, or both HPV33 and HPV59, wherein an L1 protein or immunogenic fragment thereof from one or more HPV types selected from the group consisting of HPV31, HPV45, and HPV52 is omitted from the vaccine and wherein the vaccine provides protection against cervical cancer caused by infection with the omitted HPV type.

2. The vaccine according to claim 1 wherein an L1 protein or immunogenic fragment thereof from HPV 31 is omitted from the vaccine.

3. The vaccine according to claim 1 wherein an L1 protein or immunogenic fragment thereof from HPV 45 is omitted from the vaccine.

4. The vaccine according to claim 1 wherein an L1 protein or immunogenic fragment thereof from HPV 52 is omitted from the vaccine.

5. The vaccine according to claim 1 wherein an L1 protein or immunogenic fragment thereof from HPV 31 and from HPV 45 are omitted from the vaccine.

6. The vaccine according to claim 1 wherein an L1 protein or immunogenic fragment thereof from HPV 31 and from HPV 52 are omitted from the vaccine.

7. The vaccine according to claim 1 wherein an L1 protein or immunogenic fragment thereof from HPV 45 and from HPV 52 are omitted from the vaccine.

8. The vaccine according to claim 1 wherein an L1 protein or immunogenic fragment thereof from HPV 31 and from HPV 45 and from HPV 52 are omitted from the vaccine.

9. The vaccine according to claim 1 wherein the vaccine protects against incident infection.

10. The vaccine according to claim 1 wherein the vaccine protects against persistent infection.

11. The vaccine according to claim 1 further comprising L1 proteins or immunogenic fragments thereof from HPV 58.

12. The vaccine according to claim 1 wherein at least one of the L1 proteins or fragments thereof is in the form of a virus like particle.

13. The vaccine according to claim 1 wherein at least one of the L1 proteins is a truncated L1 protein.

14. The vaccine according to claim 13 wherein the at least one L1 protein is a C terminally truncated L1 protein.

15. The vaccine according to claim 1 further comprising an adjuvant.

16. The vaccine according to claim 15 wherein the adjuvant is an aluminium salt.

17. The vaccine according to claim 16 wherein the adjuvant is aluminium hydroxide.

18. The vaccine according to claim 15 wherein the adjuvant is 3D MPL.

19. The vaccine according to claim 15 wherein the adjuvant is 3D MPL and aluminium hydroxide.

20. A method to protect a patient against infection caused by HPV 16, HPV 18 and at least one other HPV type selected from the group consisting of HPV 31, HPV 45 and HPV 52, the method comprising administering the vaccine of claim 1 wherein the vaccine provides protection against infection caused by the omitted HPV type.

21. The method of claim 20 wherein the omitted HPV type is HPV 31.

22. The method of claim 20 wherein the omitted HPV type is HPV 45.

23. The method of claim 20 wherein the omitted HPV type is HPV 52.

24. A method to prevent or reduce the frequency of cytological abnormalities in a patient caused by HPV 16, HPV 18 and at least one other HPV type selected from the group consisting of HPV 31, HPV 45 and HPV 52, the method comprising administering the vaccine of claim 1 wherein the vaccine prevents or reduces the frequency of cytological abnormalities caused by the omitted HPV type.

25. The method of claim 24 wherein the omitted HPV type is HPV 52.

26. The method of claim 24 wherein the omitted HPV type is HPV 45.

27. The method of claim 24 wherein the omitted HPV type is HPV 31.

28. A method to prevent the formation of histologically-confirmed CIN lesions caused by HPV 16, HPV 18 and at least one other HPV type selected from the group consisting of HPV 31, HPV 45 and HPV 52, the method comprising administering the vaccine of claim 1 wherein the vaccine prevents the formation of histologically-confirmed CIN lesions caused by the omitted HPV type.

29. The method of claim 28 wherein the omitted HPV type is HPV 52.

30. The method of claim 28 wherein the omitted HPV type is HPV 45.

31. The method of claim 28 wherein the omitted HPV type is HPV 31.

32. A method to prevent or reduce the frequency of cytological abnormalities in a patient caused by oncogenic HPV types, the method comprising administering the vaccine of claim 1.

33. A method to prevent the formation of histologically-confirmed CIN lesions in a patient caused by oncogenic HPV types, the method comprising administering the vaccine of claim 1.

34. A method to manufacture the vaccine of claim 1, the method comprising combining L1 proteins or immunogenic fragments thereof from HPV 16, HPV 18 and at least one other oncogenic HPV type, wherein the vaccine does not comprise an L1 protein or immunogenic fragment thereof from one or more HPV types selected from the group consisting of HPV 31, HPV 45, and HPV 52.

* * * * *